United States Patent [19]

Rabito et al.

[11] Patent Number: 5,301,673
[45] Date of Patent: Apr. 12, 1994

[54] AMBULATORY CLEARANCE FUNCTION MONITOR

[75] Inventors: Carlos A. Rabito, Medford; Richard H. Moore, Concord, both of Mass.

[73] Assignee: Massachusetts General Hospital, Boston, Mass.

[21] Appl. No.: 793,781

[22] Filed: Nov. 18, 1991

[51] Int. Cl.$^5$ .............................................. A61B 6/00
[52] U.S. Cl. ................................. 128/659; 128/633; 128/665
[58] Field of Search ...................... 128/654, 659, 653.1, 128/653.4, 662, 664, 665, 633; 354/39, 40, 41

[56] References Cited

U.S. PATENT DOCUMENTS

| | | | |
|---|---|---|---|
| 3,827,427 | 8/1974 | Knoll | 128/659 |
| 4,092,980 | 6/1978 | Frank et al. | 128/654 |
| 4,243,884 | 1/1981 | Avera, Jr. | 128/654 |
| 4,329,986 | 5/1982 | Babb | 128/654 |
| 4,380,240 | 4/1983 | Jobsis et al. | 356/41 |
| 4,682,604 | 7/1987 | Fymat et al. | 128/659 |
| 4,798,955 | 1/1989 | Rosenthal | 128/633 |
| 4,889,991 | 12/1989 | Ramsey et al. | 128/659 |
| 4,893,013 | 1/1990 | Denen et al. | 128/659 |
| 4,908,202 | 5/1990 | Schultz . | |
| 5,054,915 | 10/1991 | Kanda et al. | 356/39 |
| 5,154,176 | 10/1992 | Kanda | 128/665 |

FOREIGN PATENT DOCUMENTS

| | | |
|---|---|---|
| 82300522.8 | 2/1982 | European Pat. Off. . |
| 86302549 | 4/1986 | European Pat. Off. . |
| 2641039 | 9/1976 | Fed. Rep. of Germany . |
| 3245778 | 6/1984 | Fed. Rep. of Germany . |

OTHER PUBLICATIONS

Rossing, et al., "The Glomerular Filtration Rate Determined with Tc-DTPA and a Portable Cadmium Telluride Detector", 1978, Scand. Jour. Clin. Lab. Invest., vol. 38, pp. 23-28.

Casey et al., "GFR Measurement by Simulating Constant Infusion with Data Acquired Using a CdTe Detector, A Feasbility Study", 1986, Nuclear Med. Communications, vol. 7, pp. 811-818.

Bak et al., "Optimal CdTe-Detector Mounting for Evaluation of the Kidney Function with $^{99m}$Tc-DTPA", 1982, Proc. III World Congress of Nuclear Medicine and Biology, Paris, pp. 609-613.

Blaufox, et al., "Measurement of Effective Renal Plasma Flow in Man by External Counting Methods", 1967, Jour. Nucl. Med., vol. 8, pp. 77-85.

Earle, et al., "A Simplified Clinical Procedure for Measurement of Glomerular Filtration Rate and Renal Plasma Flow", 1946, Proc. Soc. Exp. Biol. Med., vol. 62, pp. 262-269.

(List continued on next page.)

Primary Examiner—Lee S. Cohen
Assistant Examiner—Samuel Gilbert
Attorney, Agent, or Firm—Choate, Hall & Stewart

[57] ABSTRACT

Accurate and continuous monitoring of clearance function is obtained by determining the depletion of a labelled substance from the extracellular body fluid using an external monitor which detects label from within a defined tissue volume. The detector of the external monitor is contained within a collimator which functions to both exclude external influences and to functionally isolate the volume of extracellular fluid to be monitored. Also, a method for determining and expressing a clearance function in a subject includes steps of allowing a time sufficient to permit establishment of equilibrium of a detectable substance in the extracellular space in the subject, obtaining first and second measures, at first and second times, of the detectable substance in the extracellular fluid within a defined tissue volume in the subject, and determining the slope of the measures over the time interval.

7 Claims, 3 Drawing Sheets

OTHER PUBLICATIONS

Sapirstein, et al., "Volumes of Distribution and Clearances of Intravenously Injected Creatinine in the Dog", 1955, Am. Jour. Physiol., vol. 181, pp. 330-ff.

Chantler, et al., "Estimation of Glomerular Filtration Rate From Plasma Clearance of 51-Chromium Edetic Acid", 1972, Arch. Dis. Child, vol. 47, pp. 613-ff.

Carrie, et al., "Creatinine: An Inadequate Filtration Marker in Glomerular Diseases", 1980, Am. Jour. Med., vol. 69, pp. 177–182.

Shemesh, et al., "Limitations of Creatinine as a Filtration Marker in Glomerulopathic Patients", 1985, Kidney Int., vol. 28, pp. 830–838.

Walser, et al., "Creatinine Measurements Often Yield False Estimates of Progression in Chronic Renal Failure", 1988, Kidney Int., vol. 34, pp. 412–418.

Price, "Comparison of Creatinine Clearance to Inulin Clearance in the Determination of Glomerular Filtration Rate", 1972, Urology, vol. 107, pp. 339–340.

Bojsen, et al., "Portable Cadmium Telluride Detectors and Their Applicability for External Measurement of $^{51}$Cr-EDTA Clearance*", 1981, *Intl. J. Applied Radiation and Isotopes*, vol. 32, pp. 719–727.

Cerretelli, et al., "Cadmium Telluride $^{133}$Xe Clearance Detector for Muscle Blood Flow Studies", Feb. 1978, *IEEE Transactions on Nuclear Science*, vol. NS-25, No. 1, pp. 620–623.

AMBULATORY CLEARANCE FUNCTION MONITOR

BACKGROUND OF THE INVENTION

This invention relates to monitoring organ function. One function of some organs, such as for example the kidney or the liver, is removal of substances from body fluids. The performance of such a clearance organ can be determined by assaying for accumulation in body fluids of a substance that is expected to remain constant or to deplete, or by monitoring the clearance by the organ of a labelled substance from the body fluids, for example.

The kidney is one such clearance organ that removes substances from body fluids. Acute renal failure ("ARF") as a complication of medical, obstetrical and multiple surgical conditions represents an important health problem. Currently patients suffering from ARF have a survival rate of about 50%. The pathogenesis of renal failure remains undefined, and there are no clear approaches for its prevention and treatment. In the early stages of renal failure patients show no symptoms and feel no discomfort. Diagnosis can be made by analyzing the body fluids to determine whether the kidneys are maintaining the expected levels of one or more substances.

Because of the abruptness of the renal impairment in patients having ARF, their clinical status following the onset of renal failure is determined largely by their prior state of health and the nature of the insult that led to the renal failure. Hypoperfusion of the kidney is a frequently recognized insult leading to ARF in the setting of trauma, surgery, hemorrhage or dehydration. Continuous and precise monitoring of the cardiopulmonary function in such settings has long been available and has helped in restoring the normal circulatory status of the acute patient, but estimation of the renal function conventionally is carried out by such relatively crude means as measurement of urine output and determination of plasma creatinine level. Such standard methods are inadequate for monitoring renal function in the acute patient.

Although the kidney is capable of virtually complete recovery after an episode of hypoperfusion, transient ischemia or toxin-induced cellular destruction can suppress urine formation for days or even weeks. Current methods of measuring renal function have poor time resolution, and undetected or late-detected renal failure accounts for substantial mortality. There is at present no reliable method for continuous and near real-time monitoring of renal function.

Renal function is conventionally determined by measuring the levels of substances in the urine or the serum, or both. Either technique can be made quantitative, but they have not become widely used for monitoring because, among other reasons, they require taking multiple samples from the patient and the sample analysis is time-consuming and costly.

Renal function is commonly assayed by determining creatinine levels in the urine or serum (Carrie et al., 1980, *Am. Jour. Med.*, Vol. 69, pp. 177 ff.; Shemesh et al., 1985, *Kidney Int.*, Vol. 28, pp. 839 ff.; Walser et al., 1988, *Kidney Int.*, Vol. 34, pp. 412 ff.; Price et al., 1972, *Urology*, Vol. 107, pp. 339 ff.). However, measurement of serum creatinine or of creatinine clearance may not provide an accurate measure of glomerular filtration rate.

In one accurate but technically difficult approach to determining clearance rate, a substance is introduced to the patient by continuous intravenous infusion until an equilibrium is reached at which the plasma level of the substance (as determined by analysis of plasma samples) is steady, at which point the infusion rate is equal to the rate of loss in the urine (Earle et al., 1946, *Proc. Soc. Exp. Biol. Med.*, Vol. 62, pp. 262 ff.)

In another approach, the glomerular filtration rate is calculated from an analysis of the rate of disappearance of a labelled substance from the plasma after a single intravenous injection. Following an equilibration period, the clearance of the labelled substance is determined by measuring the level of the label remaining in a series of blood samples taken over a period of several hours; the injected substance can be radiolabelled and the amount of the radiolabel detected in the samples (Sapirstein et al., 1955, *Am. Jour. Physiol.*, Vol. 181, pp. 330 ff.; Chantler et al., 1972, *Arch. Dis. Child.*, Vol. 47, pp. 613 ff.) or the quantity of the substance remaining in each of the series of blood samples can be determined by gas chromatography after extraction of the substance from the serum (H. -U. Schulz, 1990, U.S. Pat. No. 4,908,202). The non-endogenously produced substance inulin may be an ideal filtration marker for GFR determination, and it has remained the "gold standard". Because inulin is in limited supply and difficult to measure, alternative substances have become the choice for routine use, particularly $^{51}$Cr-EDTA, $^{99m}$Tc-DTPA and $^{125}$I-sodium iothalamate.

External monitors for measuring renal function have been suggested, but have not come into wide use for a variety of reasons. In the suggested approaches, a radiolabelled substance is administered to the patient, and then a radiation detector is positioned so that it is exposed to radiation from the labelled substance in the blood or urine. External monitors have been positioned adjacent the head, and on the chest of the patient to be monitored, to bring the detector near the blood stream; or adjacent the kidney or urinary bladder, to bring the detector near the urine. The proposed apparatus can be expensive, patient movement can be restricted during monitoring, the patient can be uncomfortable during monitoring, and background noise generally limits the accuracy and reliability of the measurements.

In one such approach, Blaufox et al., 1967, *Jour. Nucl. Med.*, Vol. 8, pp. 77–85, describes measuring clearance of $^{125}$I-hippurate using an external counter aimed at the zygomatic arch of the skull, and requires two blood samples for monitor calibration. This approach has the disadvantage that the patient must be immobilized while the apparatus is in use, and development of a helmet containing the monitor and recorder is suggested as a means for providing some patient mobility during monitoring.

Rossing et al., 1978, *Scand. Jour. Clin. Lab. Invest.*, Vol. 38, pp. 23–28; and Casey et al., 1986, *Nucl. Med. Comm.*, Vol. 7, pp. 811–818, describe using external detectors placed upon the patient's chest to determine the clearance of $^{99m}$Tc-DTPA from the blood as a measure of renal function. In these approaches, one plasma sample is taken in order to convert the external rate constant to plasma clearance. Because the background noise to signal ratio is fairly high, and renal function, as expressed by GFR, can be determined by taking the slope of the data values at intervals longer than about 30 to 60 minutes.

Bak et al., 1982, Proc. III World Congress of Nuclear Medicine and Biology, Paris: 1982, pp. 609-13, describes positioning a CdTe detector at the back of the leg 10 cm below the knee for analyzing $^{99m}$DTPA clearance as a measure of renal function.

In another approach, Junges German Patent No. 3,245,778 describes using a gamma camera with three detectors, one focused on each kidney and the third on the urinary bladder, to measure quantity of a radiolabelled substance removed by the kidneys.

SUMMARY OF THE INVENTION

We have discovered that clearance of a substance from a subject's body, or from a portion of a subject's body, can be continuously and accurately monitored by using an external monitor arranged to detect the presence of the substance within a defined tissue volume to determine the depletion of the substance.

For example, the glomerular filtration rate can be monitored in a patient by administering to the patient a detectable filtration marker, and then at intervals of time detecting the presence of the filtration marker in the extracellular fluid within a defined tissue volume. The filtration marker is a substance that is cleared from body fluids by the normal kidney. A radiolabelled substance, for example, can be used as a filtration marker, and the tissue volume can be defined, for example, by arranging a collimator, radiopaque at least to the energy sensed by the detector as indicating the presence of the labelled substance, to enclose a portion of the patient's body, such as a portion of the upper arm; and the presence of the labelled substance within the defined tissue volume can be detected by arranging a detector so that it responds substantially only to sensed energy from such of the labelled substance as is in the extracellular fluid within the enclosed body portion.

The monitor of the invention is lightweight and compact and is easily worn by the patient, and the patient can be free to move about during clearance function monitoring according to the invention. The invention thus provides for near real-time continuous monitoring of the clearance function in ambulatory patients as well as immobilized patients.

In general, in one aspect, the invention features a method for monitoring a clearance function by determining the depletion of a detectable substance from the extracellular body fluid, including arranging a detector so that the detector responds to substantially only such of the detectable substance as is within a defined tissue volume.

In preferred embodiments the detector specifically responds to radiant energy from the detectable substance. In some preferred embodiments the detectable substance is radioactive, and the detector includes a radiodetector; or, the detectable substance is fluorescent, and the detector includes a photodetector. The radiodetector can be a scintillator such as, for example, a NaI, CaF, CaI, or BaF detector; or the detector can be a non-scintillating detector such as, for example, a CdTe detector, or any solid, gas, or liquid type radiodetector as appropriate for the particular radiation to be detected.

In preferred embodiments a barrier, substantially opaque to the specifically detectable radiant energy, at least partly defines the defined tissue volume from which the specifically detectable radiant energy can reach and be detected by the detector. In some embodiments the barrier includes an aperture that defines a range of directions the specifically detectable radiant energy can take to reach the detector; and in some embodiments the barrier includes a barrier enclosing the body portion.

In some preferred embodiments the detectable substance is injected into the subject, for example intravascularly. Following injection at a particular intravascular site, the labelled substance becomes progressively more uniformly distributed in the blood, and begins to pass from the intravascular space to the extravascular space. And, clearance of the labelled substance commences when fluid carrying the substance reaches the clearance organ or clearance organ system. Some time after the initial injection, the concentration of the substances reaches an equilibrium in the fluids within the intravascular and the extravascular spaces. The intravascular and extravascular spaces are together referred to here as the extracellular space, and the fluids within the extracellular space are together referred to here as the extracellular fluid. For a substance such as $^{99m}$Tc-DTPA, for example, useful for determining glomerular filtration rate, the equilibration of the substance within the extracellular space of the upper arm of an adult requires about 15 to 20 minutes' time. Once equilibrium is reached, the extracellular fluid concentration of the substance and, hence, the intensity of the label, falls at a rate dependent upon the rate of the clearance function.

Preferably, the substance is radiolabelled, and a radiation detector is positioned adjacent a limb and within a substantially radiopaque barrier encircling a portion of a limb, so that radiation substantially only from label within the enclosed body portion reaches the detector.

In preferred embodiments the labelled substance includes a radiolabelled agent which is cleared substantially only by the organ whose clearance function is to be monitored, such as for example $^{99m}$Tc-DTPA, $^{51}$Cr-EDTA, $^{125}$I-iothalamate and $^{125}$I-hippurate for determining kidney function; the radiopaque barrier is made of lead or a lead containing composition and is configured at least in part to form a cylindrical enclosure about a body portion such as a portion of a limb, for example the upper arm, and the soft tissues of the body portion are compressed slightly to ensure an approximately constant extracellular fluid volume in the enclosed space during the monitoring period.

In some preferred embodiments the detector is provided with signal processing and display means for computing and indicating a measure of the clearance function, and more preferably with means for recomputing the measure and updating the display at intervals. The signal processing means can report the measure of clearance function in near real-time, that is, it can update the clearance function measure in short time intervals, for example in the order of several minutes; or the signal processing means can store sampling information continuously or at sampling intervals for later retrieval and analysis. The signal processing means can include means for selecting a sampling interval, for example, a counting interval for radiation detection; preferably the duration of the sampling interval can be preset or can be varied over the course of the monitoring period, and more preferably it can be increased as necessary to provide for a calculation of the clearance rate within a desired statistical confidence limit.

In some embodiments the apparatus includes a plurality of detectors; the detectors can be adapted to detect different detectable substances, or to provide replicate samples of detection of a single detectable substance.

In another aspect the invention features apparatus for monitoring a clearance function in a person, including a detector sensitive to a label on a labelled substance in a body fluid, and a first barrier adapted as an aperture to define generally a direction from which the label can be detected by the detector. In preferred embodiments, a second barrier is adapted to enclose a portion of the person's body and arranged so that the detector is sensitive substantially only to label within the enclosed body portion.

The collimator substantially prevents any signal from outside the enclosed body portion from being sensed by the detector, and defines a volume of extracellular space within the enclosed body portion from which the signal can be sensed by the detector.

In preferred embodiments the monitoring apparatus further includes an electrical power source; signal processing means responsive to the detector; and means responsive to the signal processing means for displaying a measurement related to the clearance rate.

In preferred embodiments the detector is a cadmium telluride or sodium iodide radiation detector; the collimator includes a support made of molded plastic in the shape of a hemicylinder and a flexible sheet made of vinyl lead that can be wrapped around a portion of the person's body to form a generally cylindrical radiopaque shield.

In some preferred embodiments the signal processing means includes a microprocessor, preferably programmed to achieve a desired confidence level, which collects data from the detector over a selected time interval, typically 60 seconds, to obtain a measurement of the label, calculates a clearance rate based upon a comparison of successive label measurements levels, and estimates the error. The organ function is preferably displayed as a rate constant, having units of $min^{-1}$, with an error estimation; and successive label measurements are made and the display is updated at 2-5 minute intervals. A preferred power source is a rechargeable battery having sufficiently low voltage to provide safety, and is capable of powering operation for many hours.

In another aspect, the invention features a method for expressing a clearance function as a rate constant, in units of $min^{-1}$. Unnormalized GFR correlates less well with the clearance rate constant ($r^2=0.8049$, $P<0.05$). The clearance rate constant for renal function as determined according to the invention by $^{99m}Tc$-DTPA clearance, for example, correlates well with glomerular filtration rate, normalized to body surface area, and it thus provides an accurate determination of renal function while avoiding any need for potentially inaccurate calculations based upon estimated body surface area.

The invention can be used to monitor clearance function in a variety of settings including, surgery, drug titration, organ transplants, early diabetes detection, cardiac failure, and septic shock.

Once the initial injection of labelled substance has been made and the apparatus according to the invention has been set up on a patient, the clearance function can be continuously monitored even while the patient is ambulatory, and the monitoring can be carried out in the absence of strict medical supervision.

DESCRIPTION OF PREFERRED EMBODIMENTS

GENERAL DESCRIPTION

Structure, generally

Generally, a clearance function monitor according to the invention includes a detector, positionable on the body surface or positionable noninvasively in a body cavity, that is capable of detecting the presence of a detectable substance in adjacent and proximate tissues, and includes means for defining a tissue volume within which the detectable substance can be so detected. The detector is sensitive to energy radiating from the detectable substance, and the means for defining the tissue volume can include a barrier, substantially opaque to the radiation, that forms an aperture limiting the direction from which the energy can pass to the sensible part of the detector. For example, the detector can be a radiodetector and the detectable substance can be radioactive; and the barrier can include a collimator, generally surrounding the detector and having an opening that permits the detectable radiation to pass. The geometry and dimensions of the aperture in relation to the sensible portion of the detector generally determines the shape and dimensions of the space from which detectable radiation can reach the detector. It will be appreciated that not all radiation reaching the detector by way of the aperture will have followed an undeflected course from the detectable substance; but, generally, less deflected radiation can be expected to have a higher energy at the detector than more deflected radiation. It will also be appreciated that the capacity of the radiation to pass through the tissues depends, among other factors, upon the initial energy and type of the particular radiation, and upon the opacity of the tissues to the particular radiation. Thus, a further limit on the dimensions of the space from which detectable radiation can reach the detector (that is, a further limit on the defined tissue volume) can be provided, for example, by using a discriminator to reject radiation reaching the detector below (or above) a selected threshold energy level. The effect of these approaches is to substantially exclude scattered radiation from detection.

The means for defining the tissue volume may include, as an alternative or in addition to an aperture as described generally above, a barrier, substantially opaque to the radiation, for at least partly enclosing a portion of the subject's body containing the defined tissue volume to be sampled. For a radioactive substance and a radiodetector, this body-part enclosing barrier can be a radiopaque sheet, such as a flexible lead composition, that can be affixed in a generally cylindrical configuration about a portion of a limb of the subject; the detector can be situated within this enclosing barrier (or an opening in the barrier can be provided for passage of the radiation to the sensible part of the detector).

An embodiment of the invention, namely a monitor adapted for measuring the clearance rate of a radiolabelled substance from the patient's extracellular fluid, is described below by way of example.

STRUCTURE, RENAL FUNCTION MONITOR

Figure 1:
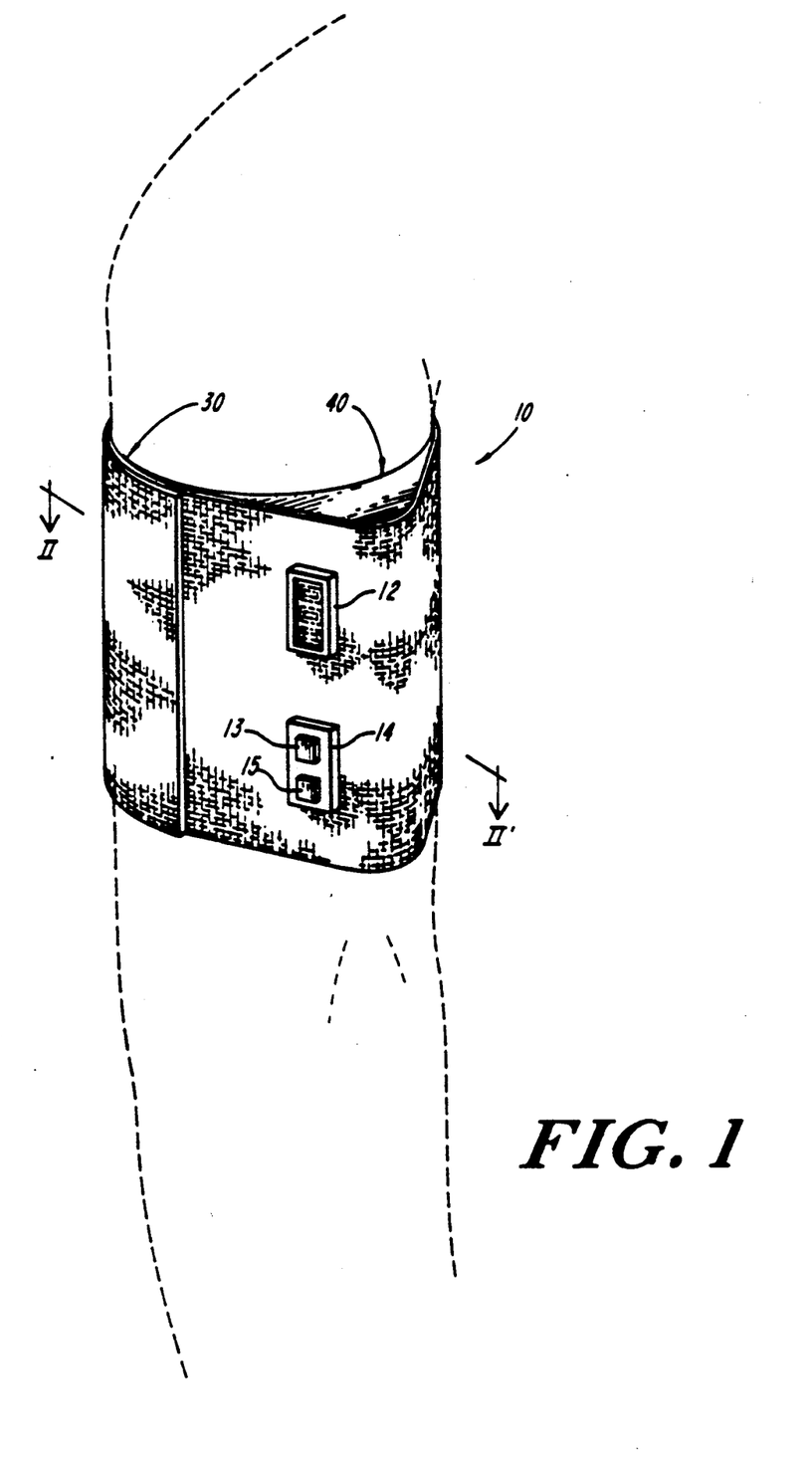
FIG. 1 is a perspective view of a clearance function monitor of the invention, showing the apparatus in place on an upper arm of a patient.
Figure 2:
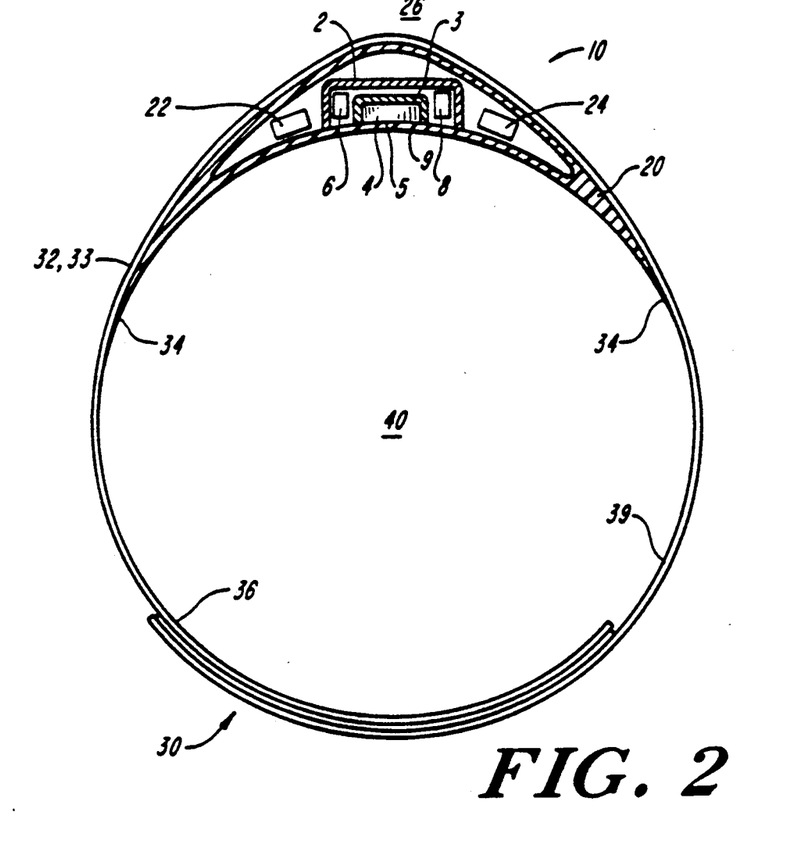
FIG. 2 is a sectional view thru the apparatus of FIG. 1, showing positions of the various components.
Figure 3:
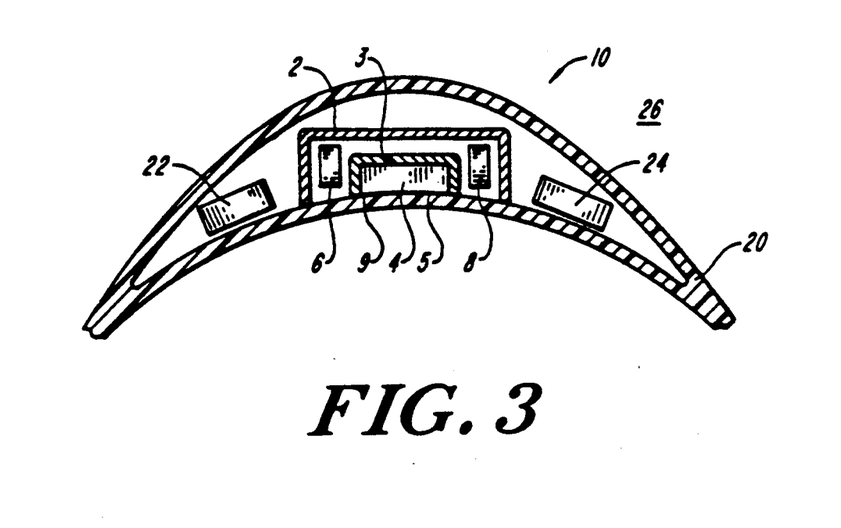
FIG. 3 is a sectional view thru the apparatus of FIG. 1, showing an enlargement of the portion within the broken circle in FIG. 2.

An external monitor according to the invention, of the kind having a collimator forming an aperture in addition to a body-part enclosing barrier, is shown by way of example in place on a patient's upper arm in perspective view in FIG. 1, in sectional view in FIG. 2, and in a more detailed sectional view in FIG. 3. The apparatus generally includes detector instrumentation carried in an instrumentation housing, shown generally at 10, and a flexible cuff, shown generally at 30 wrapped about and enclosing a generally cylindrical portion 40 of the patient's upper arm. A digital display, shown generally at 12, and a control console, shown generally at 14, including an on/off switch 13 and a microcomputer reset switch 15, are mounted in a readily accessible place on an outer surface of the instrumentation housing 10.

With reference now also to FIG. 2, the detector and associated electrical power supply and instrumentation are mounted in a support 20 of molded plastic in the shape generally of a hemicylinder. A sheet aluminum box 2, secured within the support 20, contains radiation detector 4 and some associated signal processing devices, including preamplifier 6 and discriminator 8. Box 2 has dimensions about 1 cm×2 cm×5 cm, and is lined with a detector shielding layer 3 of lead about 2 mm thick. Detector 4 is mounted in box 2 with its sensible part 5 facing inward (that is, generally toward the center of the arm portion 40). Detector 4 is shielded by a generally cylindrical collimator 3, consisting of a layer of lead sufficiently thick to be substantially opaque to detectable radiation; an inner wall 7 of detector shield 3 is open, forming a circular opening 9 about 16 mm in diameter adjacent the sensible part 5 of the detector, and the other walls are closed. This configuration of the detector shield 3 ensures that the detector is sensible substantially only to radiation reaching the detector by way of the opening 9, forming an aperture, as described generally above.

Also encased within support 20 are a microcomputer 22 and a power source 24; these parts, and the electrical connections among them and with the controls 14 and display 12 are padded with and immobilized within the support 20 by elastomer foam 26.

A body part-enclosing barrier is formed by two sheets 32, 33 of vinyl lead, covering the outer surface of the hemicylindrical support 20 and extending beyond the edges 34 of the arch of the hemicylinder to form the skirts 36, 38 of the cuff 30.

The cuff 30, when in place as shown for example in FIGS. 2 and 3, forms a generally cylindrical barrier, enclosing (although open at the ends) a generally cylindrical tissue volume. The detector preferably is located midway the length of the cuff, that is, at approximately equal distances from the open ends. The collimator has the effect of limiting the sources of radiation that can reach the detector 4 by way of the opening 9 in the detector shielding layer 3 lining box 2; specifically the collimator ensures that the detector is sensitive substantially only to radiation from radiolabel in body fluids within the enclosed tissue volume. Although some quantity of radiation may enter the enclosed space from sources located beyond the ends of the cylinder, that is, from farther up or farther down the patient's arm, in the form of scattered radiation, that quantity is comparatively very small, and the scattered radiation represents a decreased energy at the detector, resulting in a decreased signal strength, which can be rejected by a discriminator. A preferred length for the cuff in relation to the diameter of the enclosed tissue volume depends upon the geometry and dimensions of the aperture, as discussed generally above. For example, the cuff should be long enough so that substantially no unscattered radiation can pass through the aperture in the detector shield from detectable substance (or from other sources) beyond the ends of the cuff. An overly long cuff, on the other hand, can be unnecessarily cumbersome.

Figure 4:
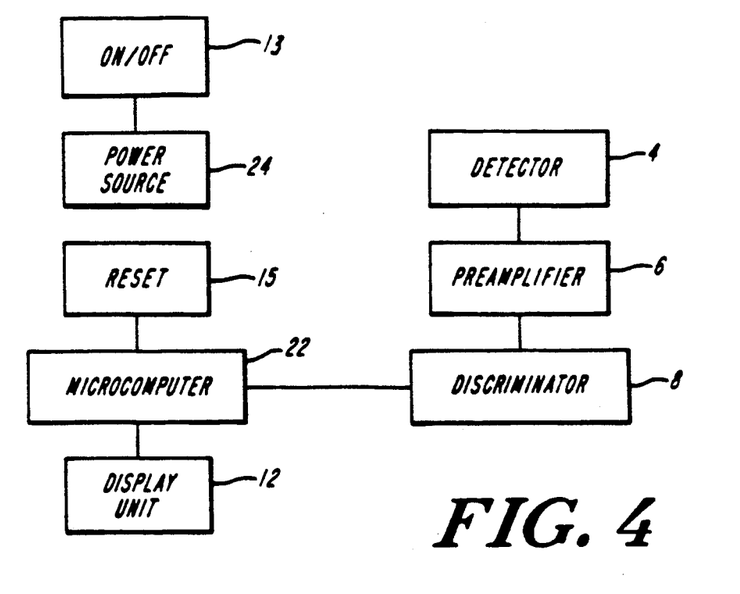
FIG. 4 is a block diagram of the electrical circuitry of a clearance function monitor according to the invention.

Referring now to FIG. 4, the data output signal from the radiation detector 4 passes through preamplifier 6 and discriminator unit 8 to microcomputer 22. Microcomputer 22 is powered by battery power source 24, which is provided with on/off switch 13, and with reset switch 15 for resetting the recording registers for information processing, as described in more detail below. The microcomputer is connected to digital display unit 12 for continuous display of the results of the data analysis, such as a clearance rate.

Figure 5:
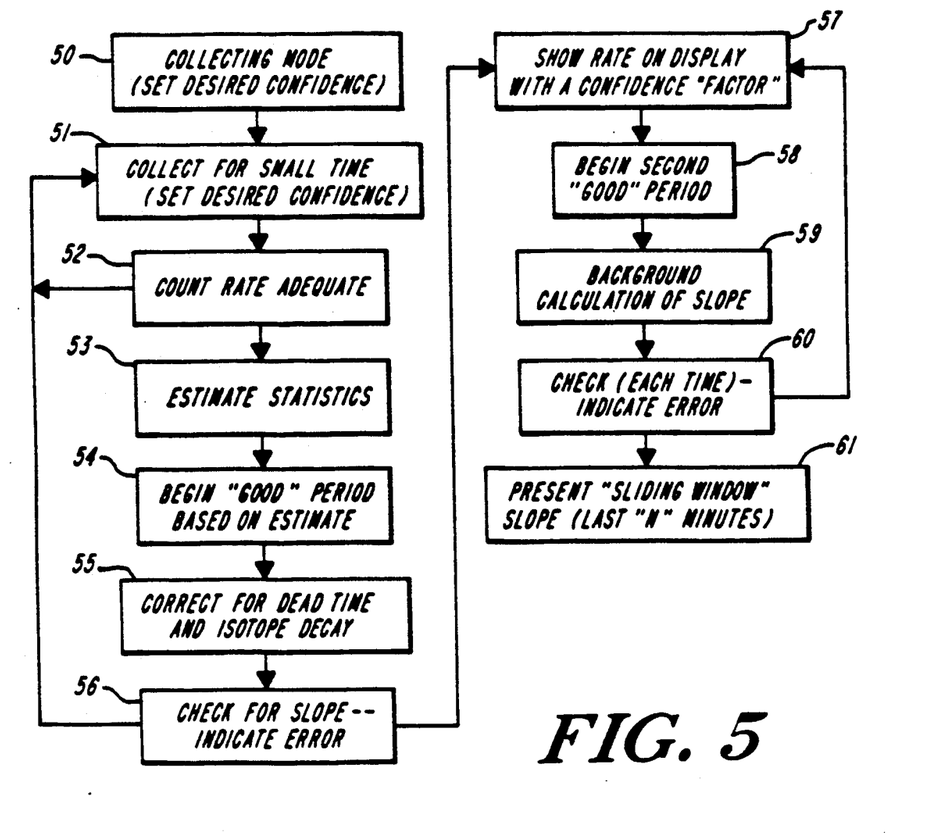
FIG. 5 is a flow diagram showing the microprocessor logic of a clearance function monitor according to the invention.

FIG. 5 shows a flow diagram of the microprocessor logic. The microcomputer uses a single compartment model, as described more fully below, to calculate the clearance function. The collection time 51 can be set for a desired collection interval, but, more preferably, the collecting mode 50 is set to a desired confidence level, and the collection time 51 is adjusted as so that the data are adequate to meet the desired confidence interval. The microcomputer monitors the count rate for data adequacy 52 by estimating the statistics 53, and then adjusts the collection time as necessary. The microcomputer then initiates a collection period 54 based upon the statistical estimate and corrects for dead time and isotope decay 55. Following the conclusion of data collection periods subsequent to the first, the microcomputer calculates and assesses the reliability of the slope, calculates the error 56 and displays the clearance rate with a confidence factor 57. The microcomputer then initiates a next subsequent data collection period 58, performs a calculation of the slope 59 and reassesses the reliability of the slope, calculates the error 60 and displays the new clearance rate with a confidence factor 57. The microcomputer continuously runs the logic cycle as long as it is on, reporting the clearance rate in the manner of a sliding time window, for so long as the level of label remaining in the extracellular fluid is high enough to provide for a statistically acceptable calculation.

USE, RENAL FUNCTION MONITOR

The method according the invention can be used for continuously monitoring the clearance of a substance from the body or from a portion of the body, and particularly from the extracellular body fluid, and thus for continuously monitoring the performance of a clearance organ or organ system, in a wide variety of settings.

For monitoring of clearance function, a monitoring session can be initiated by injecting the patient intravascularly with a labelled substance that normally is cleared by the particular organ whose performance is to be monitored. The monitoring apparatus according to the invention is affixed to the patient, for example by enclosing a part of the patient's upper arm within the cuff. Once the power is switched on, the detector and signal processor begin to collect and analyze the data reaching the detector from within the enclosed tissue space. After a period of time following the injection, typically 15-20 minutes or less, the labelled substance will have equilibrated in the extracellular space, and thereafter the depletion of the labelled substance (as recorded by progressive decline in the signal reaching the detector) provides a measure of the clearance rate. Depending upon how the microprocessor is set up, the clearance rate can be recalculated every few minutes, providing for near real-time monitoring of the clearance function.

As the labelled substance is cleared, the signal eventually falls to a level too low to provide a statistically acceptable calculation of clearance rate. At this point, a new monitoring session can be initiated by reinjecting the patient with a dose of the labelled substance, and allowing time for equilibration of the added substance in the extracellular space. If more extended monitoring is indicated, successive monitoring sessions can be initiated in this fashion a number of times, to provide for near-continuous monitoring of the organ function over a period of several days.

A preferred label for use according to the invention is a radiolabel, and the corresponding detector is a radiation detector. For monitoring renal function, for example, a labelled substance is selected that is specifically cleared by the kidneys such as, for example, $^{99m}$Tc-DTPA; and the corresponding detector is a scintillation counting device such as, for example, a cadmium telluride or sodium iodide detector.

DETAILED DESCRIPTION OF AN EXEMPLARY EMBODIMENT:

A more detailed description of an example of a renal function monitor follows, in which clearance of a radiolabelled injected substance was measured according to the detected radiation according to the invention. The performance of the apparatus was tested by comparison with results obtained using standard techniques.

DETECTOR; DATA COLLECTION

Data collection was performed using a battery-operated, pocket-size lightweight data logger having 32K total RAM (Tattletale, Model V, Onset Computer Corp., N. Falmouth, Mass.). The detector was a 16 mm diameter×2 mm thick cadmium-telluride (Cd-Te) detector (Radiation Monitoring Devices, Watertown, Mass.) connected to a preamplifier and a lower level discriminator. The detector, preamplifier and discriminator units were housed in a 1 cm×2 cm×5 cm aluminum box. The detector was enclosed in a lead shield 3 mm thick, forming a cylindrical container having a 16 mm diameter circular opening in front of the detector. The cuff was constructed over molded plastic having the shape of a hemicylinder. The aluminum box with the detector unit was secured in the center of this plastic skeleton with the sensible part of the detector facing the inside of the cylinder. The outer surface of the plastic hemicylinder was covered with a 3 mm thick generally rectangular lead-vinyl sheet. The length of the sheet exceeded by several inches the arch of the hemicylinder, forming skirts that can be wrapped about the arm of the patient, so that when positioned on the upper arm of the patient it defines a structure similar to a blood pressure cuff. Once wrapped about the arm of the patient, the cuff forms a shielded cylinder holding the detector adjacent the patient's skin and containing the detector unit within.

SOFTWARE

A basic software for the operation of the data logger provides for individually setting the counting time, and the interval between counting periods. In this configuration, the counting intervals were fixed at 59 seconds, permitting 1 second for data processing by the microprocessor within a one-minute repeat interval. The analysis software is based on a single compartment model, as discussed in more detail below.

TREATMENT PROTOCOL

All the subjects had a serum creatinine determination done the day before the study. The usual diet was not altered. Weight and height were measured soon after arrival at the treatment facility. Prior to initiation of the renal function tests, an intravenous cannula was inserted in each arm. One cannula was used for injection of radioisotopes, and the other was used for collection of blood samples. Just before a renal scintigraphic study was carried out, the ambulatory renal monitor was wrapped and secured around the arm of the patient, with the detector positioned on the outside of the arm opposite the site of injection, at the level of the deltoid insertion. The instrument was affixed to the skin using double-coated plastic adhesive tape (3M, St. Paul, Minn.). The subject then remained supine in a quiet room until the end of the studies.

RENAL SCINTIGRAPHY

A standard renal scan was performed on each patient upon arrival at the treatment facility, using a camera having a large field of view (Gemini 700, General Electric Co., Milwaukee, Wis.) having a general purpose collimator and linked to a computer. After intravenous bolus injection of $^{99m}$Tc-DTPA (0.15 mCi/Kg body weight) multiple digital and analog sequential images were obtained over a time of 32 minutes. In patients having their own kidneys, the images were acquired from the posterior projection with the camera centered at the level of the kidneys. In patients having renal transplant, the images were acquired from the anterior projection with the camera centered at the level of the pelvis. Following injection, a semiquantitative evaluation of the renal blood flow was performed by acquiring 3 second analog images over a time of 2 minutes. This was followed by static analog images (500,000 counts) at 2, 5, 10, 15 and 20 minutes to evaluate the clearance of the tracer from the renal cortex and collecting system. A computer acquisition was carried out simultaneously with the analog images. Computer acquisition of the radioangiographic phase of the study was at a rate of 2 seconds per frame for 32 frames. Static imaging was done at a rate of 30 seconds per frame for 64 frames. Regional quantitation of GFR was obtained by measuring the relative uptake of each kidney on the 2 minute static image after background subtraction.

GLOMERULAR FILTRATION RATE

The glomerular filtration rate was calculated from the clearance of $^{125}$I-iothalamate (GLOFIL-125, Iso-Tex Diagnostic Inc., Friendswood, Tex.) measured with a constant-infusion technique and timed collection of urine. Thirty minutes before the study, the subjects received orally 5 mg KI in water. After a priming bolus injection (5 to 20 uCi), a continuous infusion of $^{125}$I-iothalamate (0.3 uCi/ml saline) was given with a mini-pump (Harvard, Mini-infuser 400, Bard MedSystem Division, North Reading, Mass.) at a rate of 0.05 uCi/min for a total of 6 hours to achieve equilibrium levels close to 1,500 cpm/ml of plasma. The subjects were not permitted to eat during this period but they were encouraged to drink enough water to maintain a urine output of at least 1 ml/min. The priming dose of $^{125}$I-iothalamate was determined by considering a space distribution equal to 20% of the body weight (extracellular fluid). The dose for the subsequent infusion was calculated from the clearance of creatinine, estimated from the serum creatinine levels and considering the age, weight and sex of the subject. With this approach, the rate of excretion of $^{125}$I-iothalamate by the kidneys and the rate of infusion reach equilibrium after 90 minutes of continuous infusion. Following this equilibration period, a heparinized blood sample (5 ml plus 10 U heparin) was obtained every 30 minutes for a total of 2 to 4 additional hours. Also during this period, several urine samples were obtained by active voiding.

The activity of $^{125}$I-iothalamate in the focused solution, and in the plasma and urine samples was determined in a well gamma scintillation counter as described above. The plasma samples were counted immediately for $^{99m}$Tc-DTPA and after 3 days (to allow for a complete decay of $^{99m}$Tc) for $^{125}$I-iothalamate. Practically all the measurements of glomerular filtration rate were performed from the rate of intravenous infusion and plasma levels (plasma method). After the equilibration period, the plasma levels of $^{125}$I-iothalamate were within 5% of the mean in all but two patients. The glomerular filtration rate in these two patients was determined from the rate of urinary excretion (urine method) and plasma activity. This method, however, shows the largest variability of the two methods, probably owing to large variability in the urine collection. All calculations were standardized for body surface area.

COUNTING CHARACTERISTICS OF THE APPARATUS

To determine the intrinsic counting characteristics of the apparatus, a source of $^{99m}$TcO$_4^-$ containing between 30 and 40 uCi of activity was counted over 24 hours. The counting efficiency was set at 0.2% with the source of activity placed in front of the detector. When counts were uncorrected for physical decay of the source, the counting rate decreased at the physical half-life expected for $^{99m}$Tc. The time-activity curve was very smooth, indicating little variability in the counting rate. Calculation of the rate constant for this decay at various intervals indicated that the minimal monitoring time required for obtaining a reasonably accurate rate constant depends upon counting time. For example, when the instrument was set to count for a counting time of 9 seconds every ten seconds, the minimal recording time to obtain an accurate rate constant was about 2 minutes; when it was set to a counting time of 59 seconds every 60 seconds, the time to obtain an accurate rate constant was about 20 seconds.

POSITIONING OF THE DETECTOR

One of the basic assumptions in the use of the monitor according to the invention for measurement of GFR is that the volume and characteristic of the space probed by the detector remains relatively constant during the study. For instance, abrupt changes in the volume of this space could be reflected in rapid changes in the counting rate independent of the clearance of the agent. Because the contribution of the intravascular space to the extracellular space changes with the body location and in certain regions (precordial) with the cardiac cycle, the characteristic of the counting rate was determined with the detector placed upon various parts of the body. Large and rapid changes in the counting rate appeared with the detector placed in the precordial region. With the detector placed over the liver, less extreme changes appeared; but the urinary bladder, itself containing a substantial and varying level of label, is nearby, especially when the patient is sitting, and thus contributes to the detected activity. The arm provided the most consistent recording of activity over time; a substantial isolation from extraneous signal can be achieved when the cuff is placed about the upper arm. Moreover, contrary to what is normally expected from the multiple blood sample collection technique, the decrease in activity over time as determined according to the invention, in which the detector is sensitive to label within a defined volume of tissue space containing a defined volume of extracellular fluid, represents the clearance of the agent from a single compartment.

MONITORING OF THE RENAL FUNCTION

To determine the value of the invention for monitoring of renal function, two patients at risk of ARF with serum creatinine $\geq 2$ mg/dl were monitored before, during and after an angiographic procedure. In one patient, no change in the clearance of the tracer was observed during the study, as indicated by a similar rate constant, and no changes were observed either in the urine output and serum creatinine of this patient, even 48 hours after the study. The second patient showed a significant drop in the rate of clearance, commencing during the angiographic procedure and continuing for at least 12 hours thereafter. The rate constant, as measured according to the invention, decreased in this patient from $2.85 \times 10^{-3}$ min$^{-1}$ to $0.2 \times 10^{-1}$; and the serum creatinine in this patient increased from 2.4 to 2.8 mg/dl over the succeeding 12 hours.

The rate of clearance of $^{99m}$Tc-DTPA was also monitored in a patient in an intensive care unit. Although the initial renal function was moderately decreased as shown by a rate constant of $3.5 \times 10^{-3}$ min$^{-1}$ (Normal: $6.5 \times 10^{-3}$ min$^{-1}$), it was also relatively constant. After 5 hours there was a sudden drop in the mean arterial pressure from 97 mmHg to 57 mmHg that required appropriate therapy. Despite a rapid normalization of the blood pressure, there was a decrease in the urine output, first noticed 2 hours later. However, the monitor according to the invention detected the change in the renal function at about the time of or immediately following the hypotensive event, and prefigured the renal failure as measured by the drop urinary output.

The invention was also used to monitor the recovery of renal function in an anuric patient. The activity was relatively constant and the rate constant and urine output were close to zero at the beginning of the study. Two hours later, however, the rate constant began to increase, reaching a value 12 hours later of $1.8 \times 10^{-3}$ min$^{-1}$. This increase in rate constant was followed, with some delay, by an increase in urine output that reached a maximal value 15 hours later of about 300 ml/h.

Thus, the clearance function monitor according to the invention was capable of detecting near real-time changes in renal function, providing an indication of renal function changes earlier than other available tests. Moreover, the method according to the invention directly measures the rate constant for clearance of a glomerular filtration agent from the extracellular space, providing a direct measurement of GFR and eliminating uncertainties usually associated with determining GFR from serum creatinine and urine output.

DIRECT DETERMINATION OF RATE CONSTANT

Conventionally, estimation of GFR after a single injection of a glomerular filtration agent such as $^{51}$Cr-EDTA or $^{99m}$Tc-DTPA is made by obtaining multiple blood samples over a period of several hours. The analysis of the data considers a two compartment model, to include the clearance of the tracer from both the vascular space and the interstitial space. A single compartment model has also been used as an alternative, where the estimation of GFR is made from blood samples obtained after equilibration of the tracer in the vascular and interstitial spaces. The system equations for these models consider linear compartmental systems with constant coefficients (or rate constants $\lambda$).

For clearance from a one compartment system, in which the intravascular and interstitial spaces are considered to be a single compartment, namely the extracellular space, the system equation is:

$$\frac{dq_1}{dt} = -\lambda_{01} + I(t)$$

where:
q = Compartment size
$\lambda_{01}$ = Transport rate constant from compartment 1 to the outside (compartment 0)
t = time
I = Input function.
For an instantaneous Input (single injection):

$$I(t) = 0$$

and the solution is:

$$q_1 = q_0 e^{-\lambda_{01} t}.$$

Resolving the equation in terms of q = volume (ml) and t = 1 minute, then $q_1$ = GFR. Thus, it is clear that the value of GFR after a single injection of a glomerular filtration agent depends on the compartment size ($q_0$) and the rate constant $\lambda_{01}$. To avoid variability in GFR due to different compartment sizes, the GFR value is ordinarily corrected according to body surface area, or in other terms, $q_0$ is reduced to a standard q value. Then under this condition GFR depends only on the rate constant $\lambda_{01}$.

Thus, the estimation of the rate constant for the clearance of an "ideal" glomerular filtration agent from the extracellular space represents a direct measurement of GFR. This concept constitutes a basic principle for the use of the method according to the invention to measure and monitor the renal function.

Under ideal experimental conditions, in which a source of $^{99m}$Tc is located in the center of the cuff, and the system placed over a bench, the minimal time for obtaining accurate measurements of the rate constant can be 2 minutes or less. In the patient, however, the variability of the data owing to "biological" noise as well as to the "instrument" noise and the system equation depend largely on the location of the detector on the patient's body. For instance, when the detector is placed in the precordial area, there is a large variability in the data owing probably not only to changes in the volume, but also to the changes in the position of the cardiac chambers with reference to the detector as the patient moves about. Moreover, because in the precordial location most of the activity recorded originates in the vascular space, the equation that best describes the system corresponds to a two and not to a single compartment system. The monitor according to the invention, can reduce the "biological" noise sufficiently to allow for measurements of the rate constant at intervals of 5 minutes or less, approaching near real-time conditions, and preliminary studies performed using the invention in patients at risk of ARF showed that the instrument can accurately detect near immediate changes in renal function several hours before other parameters become abnormal.

One relative limitation in the use of the instrument to monitor renal function is that sudden changes in the volume of the extracellular space, such as, for example, hemorrhage, rapid infusion or loss of large volume of fluid, and the like, may affect the measurement of the rate constant. In such circumstances the measurements can be restarted once a new steady-state is achieved after the cardiovascular status of the patient has been stabilized.

Simultaneous use of the invention and a scintillation camera can provide not only an absolute measurement of the total renal function but also the contribution from each kidney to the total GFR.

OTHER EMBODIMENTS

Other embodiments are within the following claims.

For example, the substance can be specific for clearance by any of a variety of organs that perform a clearance function, or that metabolize a detectable substance, for example, the liver, the kidney, the thyroid, the brain or bone.

The detectable substance need not be one that is administered to the subject; it could for example be a naturally-occurring detectable substance whose quantity is indicative of a condition of the subject; or, it could be a non-naturally-occurring detectable substance, such as for example a toxin. The substance need not be a radioactive substance, detectable by a radiodetector, as described in detail above. It can be a fluorescent substance, for example, detectable by a photodetector; such a detection means can include a source of exciting radiation, and the defined tissue volume can include a body part that passes a detectable quantity of the exciting and of the fluorescing light, such as for example an earlobe or a fingertip. An example of a naturally-occurring detectable substance is creatine, useful for determining renal function, which can be detectable by its intrinsic fluorescence. And, benzene, for example, is a toxin that can be detectable by its intrinsic fluorescence. The substance need not be an organic compound; for some clearance functions, for example, detection of gold, iodine or thallium can be useful.

The tissue volume to be sampled by the detector may be defined, as described above, by any one or some combination of a variety of means; for example, by using a collimator (or other barrier) that provides an aperture for passage of radiation from the detectable substance to the sensible part of the detector, or by enclosing a portion of a body part within a collimator (or other barrier); or by employing a discriminator to reject any signal having an energy that is higher than some upper limit or lower than some lower limit; or by exploiting an anatomical characteristic of the body that in and of itself limits the tissue volume within which detectable signal may be detected. As an example of the latter, a detector positioned within the ear canal and proximate the vascular bed in the ear canal can be an at least partially self limiting sampling tissue space, particularly for fluorescence-based detection.

Where a cuff is employed to assist in defining the tissue volume by enclosing a body part, attachment of the cuff to a limb or extremity is preferred over attachment to the body trunk for a variety of reasons. For example, the relatively lower vascular content of a limb provides a more linear slope after equilibration, as it is not subject to large variations in blood volume as is an organ such as the heart; and the various fluid-filled compartments in a limb are less subject to shifting position as the patient moves about. Other considerations may be pertinent, as well; for instance, the arm, and particularly the upper arm, is preferred for renal function monitoring over the upper leg, as the upper leg is too proximate the kidneys and the urinary bladder, making shielding from scattered or direct radiation from cleared labelled substance in those organs difficult; the lower leg is less preferred, although it is farther from the kidneys and bladder, because it has a low flesh to bone ratio and because the lower leg can be particularly susceptible to edema, which would change the fluid volume within the defined tissue space and interfere with accurate determination of clearance.

A substance, or a plurality of substances, can be detectable by different radiation energies; for example, two or more filtration markers can be radiolabelled using labels having two different emission energies; and two or more parameters of a single organ, or the function of two or more organs, can be simultaneously monitored. For example, one labelled substance can be one that is effective for determining GFR, and the other can be one that is effective in determining kidney perfusion rate; simultaneously monitoring these two markers, using different labels so they can be distinguished, provides information about the kidney function at the nephron level. Or, a labelled substance that is not expected to be cleared can be monitored simultaneously with a labelled substance that is expected to be cleared, and the results compared; the slope of the curve for the non-clearing substance can provide a baseline check on non-clearance related effects that alter the concentration of the detectable substance in the defined tissue volume. For example, a rapid fall in a filtration marker might indicate an increase in GFR, but a simultaneous rapid fall in the signal from a non-clearing agent might indicate an increase in overall tissue fluid, owing for example to edema, rather than to a change in GFR. The plurality of labels could be detected using multiple detectors within an external monitor or by using multiple monitors; or by using a single detector to sense multiple energy levels, and using a discriminator to resolve the signals.

What is claimed is:

1. A method for measuring depletion of a detectable substance from a subject's body, comprising
   providing a detectable substance to a subject, said detectable substance capable of equilibrating in a subject's extracellular fluid,
   allowing said detectable substance to equilibrate in said subject's extracellular fluid forming equilibrated extracellular fluid,
   situating a detector on a portion of said subject's body having a defined constant volume of said equilibrated extracellular fluid,
   enclosing said detector and said portion of said subject's body in a barrier that is substantially opaque to said detectable substance such that only said defined constant volume of said equilibrated extracellular fluid within said body portion is detected by said detector,
   measuring a response of said detector to said equilibrated detectable substance, said response indicative of the quantity of said detectable substance within said defined constant volume of said equilibrated extracellular fluid, and
   determining the depletion of said detectable substance from a change in quantity of said substance measured within said defined constant volume of said equilibrated extracellular fluid.

2. A method for measuring a clearance function of an organ in a subject, comprising
   providing a detectable substance to a subject, said detectable substance capable of equilibrating in a subject's extracellular fluid,
   allowing said detectable substance to equilibrate in said subject's extracellular fluid forming equilibrated extracellular fluid,
   situating a detector on a portion of said subject's body having a defined, constant volume of said equilibrated extracellular fluid,
   enclosing said detector and said portion of said subject's body in a barrier that is substantially opaque to said detectable substance such that only said defined constant volume of said equilibrated extracellular fluid within said enclosed body portion is detected by said detector,
   measuring a response of said detector to said detectable substance in said equilibrated extracellular fluid, said measured response indicative of the quantity of substance in said defined constant volume of said equilibrated extracellular fluid, and
   determining the organ's clearance function from a change in quantity of said substance measured within said defined constant volume of said equilibrated extracellular fluid
   wherein said detector responds substantially only to said detectable substance within said defined constant volume of said equilibrated extracellular fluid.

3. The method of claim 1 or 2 wherein said substance is detectable by detecting radiation from said detectable substance and wherein the step of situating said detector on the portion of the subject's body having a defined constant volume of said equilibrated extracellular fluid, comprises enclosing said detector within the barrier, substantially opaque to said radiation, said barrier having an opening through which said radiation passes to said detector.

4. The method of claim 3 wherein said detectable substance is radioactive and said detector comprises a radiation detector.

5. Apparatus for monitoring depletion of a detectable substance that is equilibrated in a subject's extracellular fluid, comprising a detector capable of responding to radiation from the detectable substance, a first barrier, substantially opaque to said radiation, enclosing said detector, said first barrier having an opening such that said detector will respond to substantially only the radiation from the detectable substance which enters through said opening, a second barrier substantially opaque to said radiation, enclosing said first barrier and said detector and for selectively enclosing a portion of a body part of said subject, said body portion having a defined constant volume of the extracellular fluid in which said detectable substance is equilibrated, said second barrier preventing radiation from outside said body portion to be detected by said detector, and a processing means connected to said detector and physically mounted integrally with at least one of said barriers for determining the depletion of the substance from the defined volume of extracellular fluid.

6. The apparatus of claim 5 wherein said apparatus further comprises a collimator, substantially opaque to said radiation, that surrounds said detector and permits passage of substantially only non-deflected radiation.

7. A method for determining and expressing a clearance function of an organ in a subject, comprising providing a detectable substance to a subject, allowing a time sufficient to permit establishment of equilibrium of the detectable substance in extracellular fluid in said subject, obtaining a first measure at a first time of the equilibrated detectable substance in the extracellular fluid within a defined tissue volume of the subject, obtaining a second measure at a second time of the equilibrated detectable substance in the extracellular fluid within said defined tissue volume, determining a slope of the measures over a time interval, and determining and expressing a clearance function of said subject's organ using the slope of the measures to obtain the rate of clearance of the detectable substance from the extracellular fluid by the organ.

* * * * *